United States Patent
Bachalo et al.

(10) Patent No.: US 7,252,987 B2
(45) Date of Patent: Aug. 7, 2007

(54) SYSTEM FOR ANALYSIS AND SELECTION OF ENCAPSULATED CELLULAR MATERIALS

(75) Inventors: William D. Bachalo, Los Altos, CA (US); Michael J. Fidrich, San Jose, CA (US)

(73) Assignee: Islet Technology, Inc., St. Paul, MN (US)

( * ) Notice: Subject to any disclaimer, the term of this patent is extended or adjusted under 35 U.S.C. 154(b) by 529 days.

(21) Appl. No.: 10/313,987

(22) Filed: Dec. 6, 2002

(65) Prior Publication Data

US 2003/0232425 A1  Dec. 18, 2003

Related U.S. Application Data

(60) Provisional application No. 60/338,366, filed on Dec. 6, 2001.

(51) Int. Cl.
*C12M 1/36* (2006.01)
*G01N 33/48* (2006.01)

(52) U.S. Cl. ............... 435/286.5; 435/288.5; 435/288.7; 435/308.1; 422/73; 382/133

(58) Field of Classification Search ............ 435/288.7, 435/288.5; 436/63; 422/73
See application file for complete search history.

(56) References Cited

U.S. PATENT DOCUMENTS

| | | | |
|---|---|---|---|
| 4,175,662 A | 11/1979 | Zöld | |
| 4,756,427 A | 7/1988 | Göhde et al. | |
| 5,429,821 A | 7/1995 | Dorian et al. | |
| 5,470,731 A | 11/1995 | Cochrum | |
| 5,531,997 A | 7/1996 | Cochrum | |
| 5,643,594 A | 7/1997 | Dorian et al. | |
| 5,837,200 A * | 11/1998 | Diessel et al. ................ | 422/73 |
| 5,914,262 A | 6/1999 | MacMichael et al. | |
| 5,968,820 A | 10/1999 | Zborowski et al. | |
| 6,332,540 B1 | 12/2001 | Paul et al. | |
| 6,432,630 B1 | 8/2002 | Blankenstein | |
| 6,465,226 B1 | 10/2002 | Zimmermann | |
| 2002/0115163 A1 | 8/2002 | Wang et al. | |
| 2002/0115164 A1 | 8/2002 | Wang et al. | |
| 2002/0121443 A1 | 9/2002 | O'Connell | |
| 2002/0123112 A1 | 9/2002 | Wang et al. | |
| 2002/0132316 A1 | 9/2002 | Wang et al. | |

* cited by examiner

*Primary Examiner*—William H. Beisner
(74) *Attorney, Agent, or Firm*—Patterson, Thuente, Skaar & Christensen, P.A.

(57) ABSTRACT

Capsules, entrained in a fluid medium, are directed into a channel deflection system designed to enable evaluation and separation of successfully encapsulated cellular material from the blanks and other debris. Preferably, the fluid media with the capsule is introduced into a first or main channel and the capsules first pass one or more windows in the main channel for evaluation that is conducted by electromagnetic and/or optical means. Preferably, the evaluation results in the selection of acceptable capsules and subsequent removal of the blank capsules from the medium through the use of multiple jets that gently redirect the acceptable capsules into an alternate channel. Preferably, fluid is also introduced into the alternate channel and the main channel and the alternate channel are arranged such that there is a window defined between the two channels where the fluid flow between the two channel is directly adjacent and the jet deflection system can selectively deflect capsules across this window between the two channels with a minimum amount of force and a minimum of turbulence created in either channel.

13 Claims, 12 Drawing Sheets

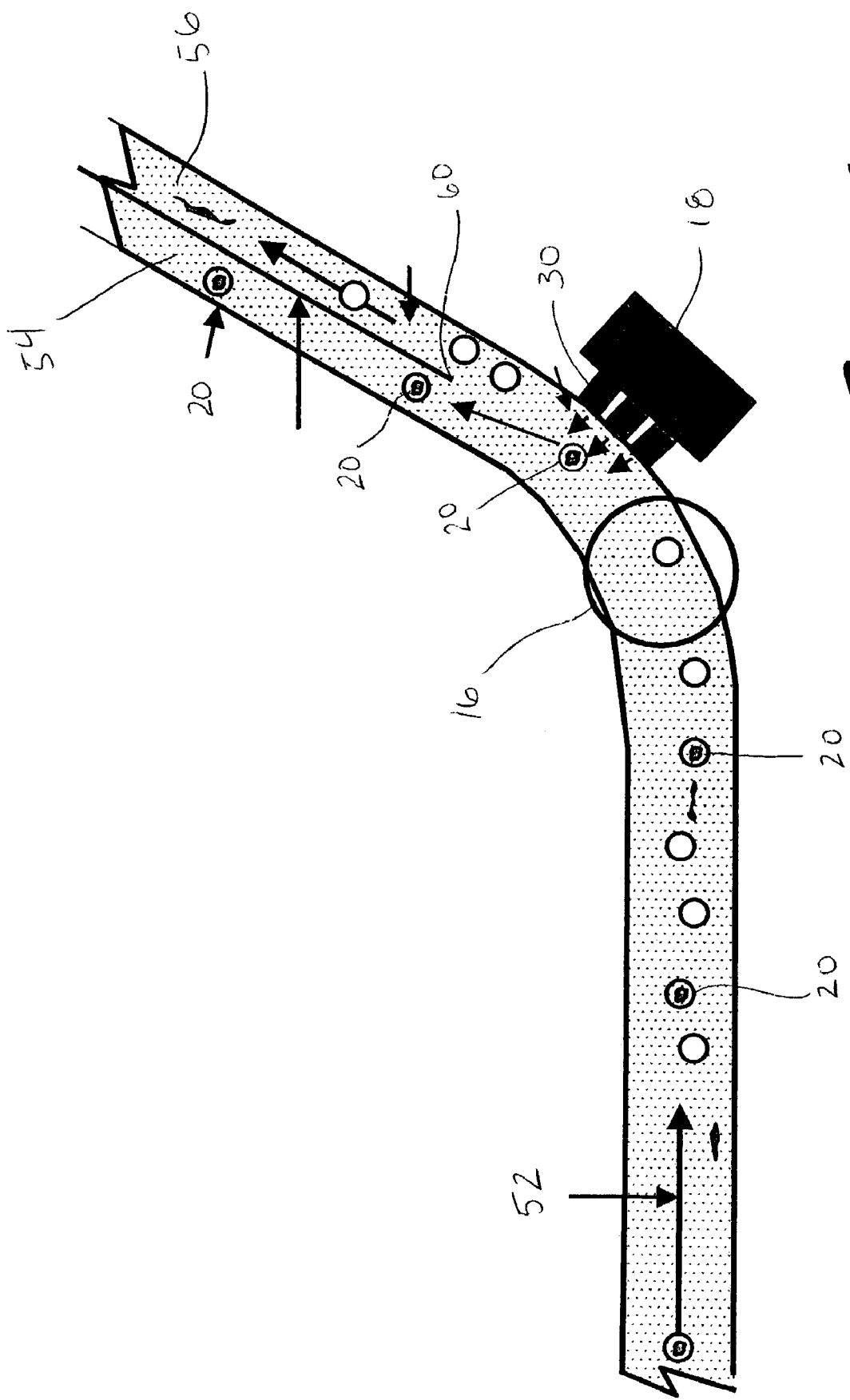

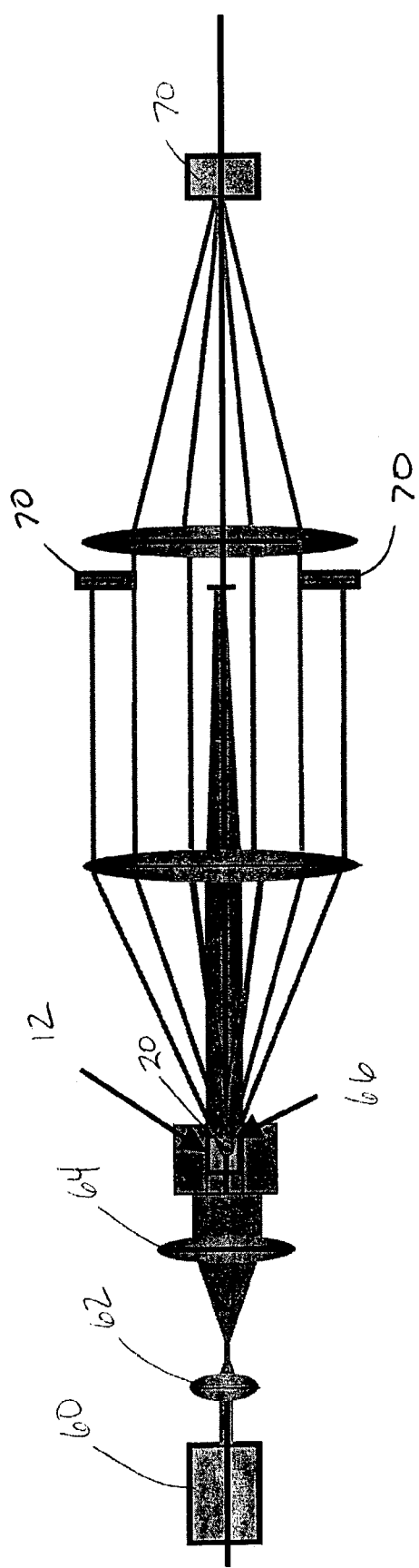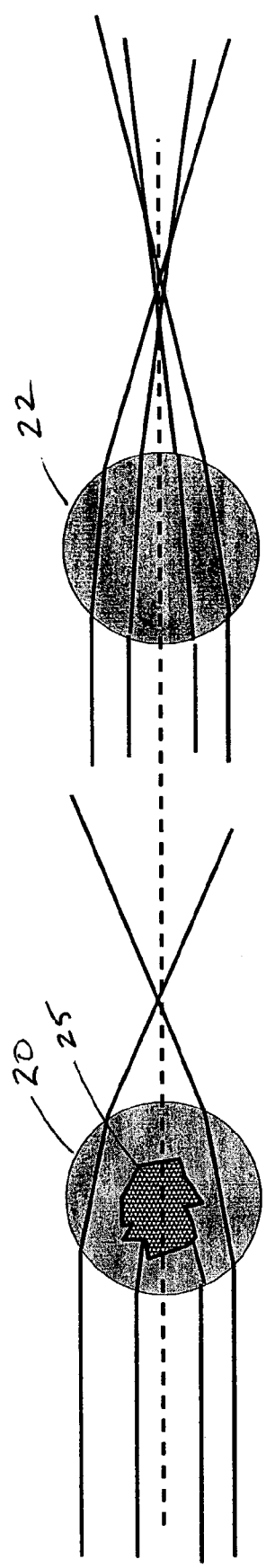
Figure 5a
Figure 5c
Figure 5b

SYSTEM FOR ANALYSIS AND SELECTION OF ENCAPSULATED CELLULAR MATERIALS

RELATED APPLICATIONS

This application claims priority from U.S. Provisional Application No. 60/338,366 entitled, OPTICAL DIAGNOSTIC SYSTEM FOR THE ANALYSIS AND SELECTION OF ENCAPSULATED ISLETS, filed Dec. 6, 2001.

GOVERNMENT GRANT

This invention was made with Government support under Contract No. N44-DK-2-2536 awarded by the National Institutes of Health, National Institute of Diabetes and Digestive and Kidney Diseases. The Government may have certain rights in the invention.

FIELD OF THE INVENTION

The present invention relates generally to system for classifying, separating and sorting particles. More particularly, the present invention relates to an automated system for analysis and selection of encapsulated cellular materials based on the quality and characteristics of the product of the cellular encapsulation technology.

BACKGROUND OF THE INVENTION

Transplantation of organ tissue into genetically dissimilar hosts has gained a significant interest in the treatment for functional deficiencies of secretory and other biological organs. For example, Type 1 insulin dependent diabetes mellitus (IDDM) remains the fourth leading cause of death by disease in the United States. There are an estimated 1 million cases of type 1 diabetics who face significant complications related to the disease and a 33% reduction in life expectancy. Recent work on islet transplantation in Edmonton, Alberta and at the University of Minnesota has generated excitement over the potential over this procedure as a treatment of the disease. Transplantation, however, generally requires the continuous use of immunosuppressive agents by the transplant recipient in order to forestall a rejection of the transplanted tissue by the recipient's immune system. Unfortunately, these immunosuppressive agents can deprive the recipient of adequate protective immune function against other diseases.

A potential solution that avoids the need for such immunosuppressive agents is the encapsulation of the tissue material so as to protect the transplanted tissue from the recipient's immune system. Micro-encapsulation of islets for transplantation presents one of the more promising methods for treating diabetes. Micro-encapsulation has demonstrated to be effective in isolating the islets from the humeral and cellular inflammatory response that occurs with diabetes, foreign tissue and material implantation. Encapsulation with a sufficiently semi-permeable protective barrier coating not only generally prevents an immune response, but also provides for an infusion of oxygen into the encapsulated material along with transfer of nutrients, ions, glucose, and hormones, as well as the excretion of metabolic waste. This maintains the health of the encapsulated tissue material.

It has been discovered that encapsulation of islets with a double coating of a cross-linkable polymer can provide substantially complete coverage of the islets in order to minimize or eliminate the possibility of adverse immune reactions, while at the same time providing a capsule having a dimension on the order of 400-500 microns. The multiple coatings of the individual capsules containing the islets serve as an additional means for assisting in the resistance to chemical, mechanical, or immune destruction by the host.

The double encapsulation process has been described by Cochrum et al. (U.S. Pat. Nos.; 5,470,731; and 5,531,997). The coating involves using non-fibrogenic alkaline earth metal alginate that is purified to be free from fibrogenic quantities of sulfate, phloroglucinol, fructose and protein moieties. A spinning cup or disk atomization technique is used to form drops with a high guluronate to mannuronate molar ratio alginate in which the islets are dispersed. Adjustments of the rotational speed and other disk atomization parameters yields the required droplet mean size and near uniform size distribution. The droplets are propelled radially outward and collected in a calcium chloride solution, which gels the drops to form the capsules. The steps are basically repeated to form the second layer. The method provides a high degree of control and reproducibility and generates several hundred thousand capsules in a few minutes.

Unfortunately, this method, like other known encapsulation techniques, does not consistently encapsulate all of the biological material without generating extra empty capsules. Not every capsule produced contains an islet, or if an islet is present, the geometry and characteristics of the capsule may be less than ideal for transplantation. Normally, there is approximately an order of magnitude more blanks (capsules without islets) than encapsulated islets in the sample. Small satellite droplets are also formed as a part of the atomization process. It is known that the encapsulation material alone in the blanks can induce an immune reaction.

For large animal transplantation, a large number of blank capsules and other debris become a problem due to the increased number of capsules required. An excessive number of blank capsules are not desirable because they may interfere with the function of the transplant and produce a greater probability of immunological attack of the graft of transplanted capsules. Where the graft may be located is also constrained by the mass of the transplant, so minimizing the extraneous material in the graft is an advantage Furthermore, because of the complexities associated with the encapsulation of such large numbers of islets (on the order of 1 million), there may be a significant number of islets that are not completely encapsulated, have an insufficient capsule wall thickness for immunoisolation, or have wall thickness that is too large for adequate diffusion of nutrients to the encapsulated tissue. Excessive capsule wall thickness adversely affects the diffusion dynamics. There is also concern with separation of the layers of encapsulation material leading to leakage. Ideally, smaller size capsules are believed to permit oxygen to better permeate into the interior of the capsule as oxygen can normally permeate up to about 200-250 microns into encapsulated tissue material.

Finally, the entire encapsulation process for islets is a time and stress sensitive process. The longer the living tissue or cells are exposed to the process or the stress is created by the encapsulation process, the less viable and effective the encapsulated tissue material will be. It has been discovered that encapsulated islets cells, for example, have a limited viability of only a few days in cell culture, both prior to encapsulation and after encapsulation and prior to transplantation. In order to obtain the approximately 1,000,000 islets needed for a human transplantation procedure any processing must be done quickly and without damage to the encapsulated islets.

The automated sorting and classifying of biological material has conventionally been performed on an individual cell level. Because of the very small size of individuals cells with diameters on the order of a few microns, it is possible to used a technique known as phoresis in which the cell absorbs some form of an electromagnetic wave so as to change the momentum or path of travel of the cell, thereby allowing cells having differing responses to the electromagnetic wave to be separated from one another. Examples of using electrical charge to separate cells (electrophoresis) are shown in U.S. Pat. No 4,175,662. Examples of using magnetic fields to separate cells (magnetophoresis) are shown in U.S. Pat. Nos. 5,968,820 and 6,432,630. Examples of using light waves to separate cells (optophoresis) are shown in U.S. patent application Ser. Nos. 2002/0115163 and 2002/0121443. While phoresis techniques work quite well for individual cells, the techniques are not scalable to larger particles because as the radius of a cellular particle increases, the mass of that cellular particle, and hence the amount of energy needed to divert that cellular particle, increases cubically. As a result, phoresis techniques are generally not applicable to cellular material having a radius of greater than about 10 microns.

More conventional mechanical and imaging techniques have been developed to work with sorting and classifying larger particles, such as pharmaceutical capsules, but such mechanical techniques are generally far too harsh for use with fragile cellular material. Because the size of most encapsulated cellular material are larger than the maximum radius for which phoresis techniques can be used, and because conventional mechanical processing techniques cannot be used, different techniques have been developed for the sorting and evaluation of encapsulated cellular material.

In one technique, aliquots of encapsulated material are sampled using image analyses systems to obtain an estimate of the size and number of the encapsulated islets. This process requires extraction of a representative sample, placing it under a microscope, photographing the image, transferring the file to the computer, and applying the image processing software to extract the desired information. The process is tedious and the sample is generally discarded so the islets are lost.

In the case of sorting empty or blank capsules from those containing cellular material, a liquid centrifugal separation technique can be used, as described, for example, in U.S. Pat. No. 6,465,226. While somewhat effective in separating blank capsules from non-blank capsules when the mass of the cellular material is significant relative to the mass of the encapsulating material as is the case in larger capsules having diameters of more than 500 microns, the forces imparted to the capsules during the centrifuge process can cause damage to the encapsulated cellular material, and the process provides no mechanism for counting or individual analysis of any of the capsules. The technique is far less effective for separating smaller capsules having diameters of less than 500 microns, however, as the mass difference between blank and non-blanks capsules is relatively smaller.

U.S. Pat. No. 6,332,540 describes an automated arrangement for separating polymeric beads from a suspension that uses a valve or rotating conduit controlled by a sensor upstream of a fork in a single fluid path in order to divert beads based to an outlet channel in response to a measurement from the sensor. Unfortunately, the turbulence created by the operation of the valve or rotating conduit can cause the separator to plug up. Any surface damage or roughness on the capsule can provide anchorage points for fibrotic overgrowth that may comprise graft function. U.S. Pat. No. 4,756,427 describes an automated arrangement for sorting particles that uses an acoustic pressure wave to divert particles in a single fluid path between a sorting branch and a waste branch in response to a sensor measurement. While more effective with relatively smaller sized particles, the acoustic pressure wave generally lacks sufficient energy to reliably deflect larger sized particles having diameters of 500 microns or greater.

U.S. Pat. No. 5,914,262 describes a number of techniques for automatically sorting encapsulated cellular material. Some of the embodiments described rely on a valve or rotating element to divert fluid from a single fluid path like the arrangement described in U.S. Pat. No. 6,332,540. Another embodiment utilizes vacuum force on a moveable probe to suck capsules onto the probe and then deposit them in appropriate wells in a microtitre plate. Still another embodiment uses a pair of opposed fluidic injectors positioned before a Y-branch in a single fluid path to deflect a capsule into one of two branches by firing one or the other of the fluidic injectors in a response to a measurement from a sensor in an arrangement similar to that described in U.S. Pat. No. 4,756,427, except that additional fluid must be pumped into the system instead of an acoustic wave being created in the fluid already in the system.

While these automated systems are generally effective for their intended purposes, the problems with these systems typically relate to damage caused to the cellular material by the forces involved in the mechanical handling of the encapsulated material and plugging or clogging of the system during repeated or extended operation. It would be advantageous to provide an automated system for evaluating and selecting encapsulated cellular materials that could permit an individual assessment of the quality of each microcapsule and allow rejection of those capsules that do not meet pre-established criteria while minimizing any significant damage to the encapsulated cellular material and still permitting high throughput with minimum disruptions.

SUMMARY OF THE INVENTION

The present invention is an automated system for evaluating and selecting encapsulated cellular material. Capsules, entrained in a fluid medium, are directed into a channel deflection system designed to enable evaluation and separation of successfully encapsulated cellular material from the blanks and other debris. Preferably, the fluid media with the capsule is introduced into a first or main channel and the capsules first pass one or more windows in the main channel for evaluation that is conducted by electromagnetic and/or optical means. Preferably, the evaluation results in the selection of acceptable capsules and subsequent removal of the blank capsules from the medium through the use of multiple jets that gently redirect the acceptable capsules into an alternate channel. Preferably, fluid is also introduced into the alternate channel and the main channel and the alternate channel are arranged such that there is a window defined between the two channels where the fluid flow between the two channel is directly adjacent and the jet deflection system can selectively deflect capsules across this window between the two channels with a minimum amount of force and a minimum of turbulence created in either channel.

In a preferred embodiment of the present invention, the double layering process as described by Walsh in U.S. patent application Ser. No. 09/900,466, creates encapsulated islets for implantation. The capsules in solution are held in a stirring vessel to keep the capsules aloft. The solution is designed to replicate the incubator conditions necessary for islet viability. From the stirring vessel the capsules are directed through flow tubes into a flow channel deflection system designed to enable evaluation and separation of the successfully encapsulated islets from the blanks and other debris. Preferably, a square channel cross-section is used to better facilitate observation and analysis. In one embodiment, flow in the channel deflection system is controlled pneumatically with a clean air supply at controlled oxygen partial pressure, which enables an operator to set pressure to the feed and collection vessels. Flow speeds range from 0.5 to 5 meters per second.

One condition limiting the flow speed is the requirement that the flow remain laminar in the channel. Hence, the flow Reynolds number is kept well below the transition value. This avoids the problems of turbulent flow creating excess shear forces on the encapsulated islets or effect the ability to deflect the encapsulated islets at the bifurcation point. The flow may be monitored using a laser Doppler velocimeter or by simultaneously monitoring the flow speed of the capsule using a double slit aperture arrangement as described.

The capsules first pass one or more windows for evaluation. The windows are positioned to enable viewing of flow behavior and for the encapsulated islet detection optical system. Preferably, diode lasers are used as a radiation light source for the interrogation but light emitting diodes or other electromagnetic radiation sources may be used. An expanded and collimated laser beam having a known beam profile is directed into the channel through the window. A slit aperture of 100 micrometers wide and two millimeters long that spans the channel cross section forms the interrogation region. The result is preferably a miniature light sheet of known geometric dimensions. Solid-state photo-detectors are used on the opposite side of the channel to detect the transmitted laser light. When a blank capsule passes the light sheet there is little or no deflection of the transmitted light so the capsule is not detected. An islet inside the capsule acts as a diffuse light scattering object so little or none of the light falling on the capsule is able to pass to the detector. Hence, a part of the laser light sheet is obscured and the detector reads a time dependent deficit in the incident laser light intensity. This deficit is seen as a negative going pulse on the oscilloscope. Threshold logic circuitry is used to detect the pulse and produce a gate signal for triggering the jet deflection system.

Preferably, a multiple jet deflection system is used at the bifurcation point downstream of the observation windows to separate blank capsules from the encapsulated islets. The valves for the jets are capable of turning on in as little as 0.25 milliseconds and can repeat at over 1,000 times per second. Since there are typically ten times as many blanks as encapsulated islets, the blanks are allowed to proceed while the jets are fired to redirect the encapsulated islets. The jets are timed to fire so as to block the progress of the islets from entering the waste channel. The solution fired by the jets is the same solution used to store the capsules. An additional window observation point may be placed along the waste channel in order to insure that only improperly formed capsules are discarded.

Beyond the basic interrogation of determining whether an islet is present, the present invention includes a number of additional evaluations through the use of laser interferometry. Additional observation windows are located in the collection channel. Observation from two orthogonal directions through the use of collimated laser light will provide a relatively complete picture as to wall thickness, size, eccentricity, and the presence of exposed tissue. The captured interferometric images containing the information of the quality of the capsules will be quickly processed (within milliseconds). This information is used to decide whether to accept or reject each islet or, in the alternative, provide a grade to each islet which will correspond with certain characteristics necessary for transplantation (e.g. perhaps a certain size islet corresponds to a certain dosage).

The evaluation system of the present invention has preferably the ability to remove 90% of the blank capsules from the sample; analyze every capsule for exposed tissue and remove faulty capsules from the sample; perform the detection and sorting operation without inducing any mechanical damage to the capsules and functional loss of the tissue; provide means to size and count all of the acceptable islets; measure the capsule wall thickness of every encapsulated islet; provide a means to sort and grade capsules based on wall thickness; surface quality and size of the capsules.

In an alternative embodiment, the present invention may also be used for the evaluation and selection of encapsulated cells for the treatment of Parkinson's disease; Epilepsy; Hemophilia; Cirrhosis of the liver; Hypothyroidism; and Addison's disease. In each case, the encapsulated cellular material preferably forms a capsule having a radius of between 10 and 500 microns.

The processes presently used to microencapsulate tissues for large animal transplants results in a large number of capsules with typically 5 to 10 blank capsules for every capsule containing the tissue. An excessive number of blank capsules are not desirable because they may interfere with the function of the transplant and produce a greater probability for immunological attack of the graft. Furthermore, because of the complexities associated with the encapsulation of such large numbers of islets (order of 1 million), there may be significant numbers of the islets that are not completely encapsulated, have insufficient capsule wall thickness for immunoisolation, or have wall thickness that is too large for adequate diffusion of nutrients to the encapsulated tissue, and they too are undesirable for the transplant. Encapsulation strategies that are currently used to overcome such problems include using double or triple encapsulations to increase the probability of ensuring adequate immunoisolation. However, the drawback is that it exposes the tissue to additional stress that may ultimately threaten the viability and functionality of the transplant and can result in excessive capsule wall thickness adversely affecting the diffusion dynamics. Ideally, if a single encapsulation could provide reliable immunoisolation, then the overall procedure is simplified and better capsule diffusion dynamics may be realized.

The present invention permits the quality of each microcapsule to be assessed and to reject those capsules that do not meet pre-established criteria. Researchers have also established that purified alginate capsules may not serve as a suitable substratum for cell attachment because mechanical imperfections on the surface of the microcapsule can provide sites for attachment and subsequent spreading of the growth from the cell anchorage. Fibrotic overgrowth is believed to be initiated once deposition of cellular material occurs. Consequently, one embodiment of the present invention includes a mechanism for rapid assessment of the surface quality of the microcapsules.

The first objective of the sorting system is that to remove blank capsules from the sample of encapsulated islets. This part of the process does not require 100% reliability since in past studies blanks have been transplanted along with encapsulated islets and, to-date; failures have not been directly correlated with an excess of blank tissue. However, the present invention is designed for 80% separation of the blanks and extraneous material from the sample in a single pass through the channel and greater than 90% separation using a dual-pass arrangement. The key requirement is to retain all of the adequately encapsulated islets that are present in the sample without subjecting the encapsulated islets to undue stress. Preferably, the present invention entrains the encapsulated tissue in a liquid media fluid at incubator conditions, such that additional time spent in the sorting system does not compromise islet viability.

The flow in the channel is preferably limited to a maximum flow speed of 5 meters/second that can be used without transitioning to turbulent flow. Higher flow speeds will allow a faster sorting rate but it may compromise the islet viability. A compromise between sorting time and stress on the sample will be developed through experimental observations. High-speed laminar flow dictates smooth inlets and surfaces in the channel to prevent tripping the flow to turbulent at high flow Reynolds number. In one embodiment, the channel is curved such that the solids in the flow are centrifuged to the outer half of the channel when they pass the interrogation window and channel bifurcation. In a preferred embodiment, the cross-section of the channel is limited in dimensions to between four to eight times the maximum radius of the capsules such that the capsules remain generally centered in the channel as a result of the equilateral buffeting of the laminar flow regions along each side of the channel operating against the capsules. In this way observations can be made to detect and eliminate secondary swirl flow in the channel cross section.

The islet detection and counting system is designed to achieve greater than 99% reliability since loss of any significant number of properly encapsulated islets is undesirable and the count provides important information for the subsequent transplant evaluation. The laser beam intensity of the detection system must be low enough to eliminate any possibility of harming the tissue. Generally, the laser intensity of the LED emitters is in microwatts, so this is not a concern.

The present invention has determined that reliable sorting of the capsules depends upon the design of the jet deflection system. Feasibility studies conducted for the present invention have shown that the valves and jets had an adequate response time and that it is possible to easily adjust all of the jet parameters including the delay, duration, and jet momentum. Although circular jets were used in the study because of the associated ease-of-fabrication, slits that span the channel to form jet sheets may also be used to produce a shorter stream wise perturbation but will not allow capsules to slip past the jets. The jets must have adequate momentum to deflect the encapsulated tissue but not have excess momentum that could damage the surface of the capsules due to impact with the channel wall. The use of multiple jets fired sequentially permits each jet to impart a smaller momentum force and still achieve the desired deflect of the capsules.

The method for sizing the islets is calibrated and evaluated using islets having a full range of morphology and sizes. This was carried out utilizing histological analyses and comparing the results. The present invention can achieve a measure of the equivalent islet diameter to within +/−10%. Preferably, the size distribution of the capsules is recorded along with the count of the number of islets in the sample.

Detection of exposed tissue requires observation from at least two orthogonal directions and possibly more angles to ensure that all such faults are detected. Feasibility studies conducted for the present invention showed that a strong indication of tissue exposure may be obtained from the laser light scattering signature. Failure detection strategies for the present invention include the use of the number of faults that are detected to determine if additional passes are warranted. If faulty capsules are missed because of orientation, a second pass will reduce the probability of detection failure since the capsule orientations at the interrogation port are completely random. Since exposed tissue will have a significant potential for exciting a fibrotic reaction in the implant of a graft, the detection and rejection of capsules having insufficient encapsulation to effectively permit immunoisolation is of great importance.

Estimating the wall thickness of each capsule was shown under feasibility studies for the present invention. All thicknesses may be measured to within +/−10 microns with the possibility of better resolution (to +/−5 microns). Observations from two orthogonal directions provides a relatively complete picture of the wall thickness, considering that the shape is spherical or quasi-spherical. Preferably, these measurements are performed inline simultaneously with the other, evaluations. The use of low-resolution CCD's, data transfer, and a fast Fourier transform (FFT) permits completion of the analysis within the time available (approximately 2 milliseconds).

The flow channel designed is preferably made from aluminum or stainless steel. All. fittings are of medical grade to ensure that no contamination is produced in the sample media. Preferably, the surfaces are polished and flat to allow sealing with the window without additional sealing material or gaskets, which may add to the risk of contamination. The flow channel deflection system is designed for easy assembly so that it may be stripped down and sterilized after each sorting run. Preferably, windows are provided at the detection region as well as downstream to allow evaluation of the sorting efficiency. A pneumatic feed system is used with precisely controlled pressure on the supply and collection vessels. Clean oxygenated air is used to supply the pressure.

Reproducing the incubator conditions within the flow channel systems helps to preserve islet viability. Preferably, the flow channel has thermostatically controlled heaters that maintain all of the components at the desired temperature. The oxygen level in the supply air is also maintained at a desired level. Computer controlled pressure sensors and regulators prevent any overpressure in the system. Control systems integrated with flow rate measurement sensors are used to maintain the relative flow rates in the waste and collection channels to optimize the sorting.

The flow rate in the channel is easily controlled by setting the pressure differential between the supply and collection vessels. In one embodiment, syringe pumps are used to drive the liquid with the encapsulated islets through the system. This approach does not easily allow the processing of larger volumes (1 to 10 liters) of the media containing the encapsulated islets. The number of capsules per cc of media must be low enough to ensure the separation between the particles is at least a few mm as they pass through the flow channel. If there is an unexpected blockage, syringe pumps can generate a very high pressure that may damage the islets. Using the pneumatic approach to driving the sample ensures that the pressure on the sample does not become excessive. Typically, a differential pressure of a few psi is adequate. A large volume liquid can be handled with minimal user intervention. Computer controlled valves and pressure transducers allow continuous monitoring of the system and accurate control of the flow in the channel. Since there are no moving parts, there is little potential for mechanical stress or damage to the sample. Preferably, the media in the channel flow as well as the media used by the jet system is kept under sterile conditions.

An electro-optical sensor system is preferably used by the present invention to enable the detection and counting of the encapsulated islets as they pass the interrogation window. Since the blank capsules are transparent and have an index of refraction only slightly greater than the media, they are essentially invisible to the appropriately designed detection system and hence, are not detected. This is significant since there are a much larger number of blanks than encapsulated islets so this relieves the load on the sorting system logic. The islets or other tissue is opaque or diffusely scatter the incident light so a strong signal is produced as they pass the interrogation window. The method only requires a low cost, low light intensity diode laser and a solid-state photo detector for the detection system. The detection electronics utilizes a signal threshold detection system that can be adjusted to only detect tissue samples larger than a specific size. The system can detect tissue samples within 10 microseconds and at a very high repetition rate (>10,000/sec) so it is not be the limiting component in the sorting system. The components are relatively inexpensive so we will place the detection systems at three locations in the channel to monitor the sorting performance and directly measure the sorting efficiency.

Using high-speed valves to form jets allows the use of the media as the fluid in the jets and permits an adequate range of deflection forces to move the selected samples into the collection channel without excess stress. With several jets lined up in the flow, each jet can contribute a part of the deflection force and hence, minimize the impact and acceleration on the capsule. The jet pressure, timing, and duration are all precisely selectable and can be optimized for adequate deflection and minimal stress on the sample. An added advantage is that their performance can be visualized to aid in optimization. It is also possible to use the valve system to provide suction on the opposite side of the channel for faster response and reduced deflection pressure on the capsules. The disadvantage of this approach is that capsules may clog the orifices. The valves are relatively inexpensive and have along life expectancy.

Feasibility studies using the present invention have demonstrated that it is possible to count and size the islets inline. The method may be applied from two directions to obtain an equivalent diameter (islets are not spherical so a true size definition would require more than one dimension) from two orthogonal projections. Considering that islet equivalents are defined in terms of diameter based on a small "representative sample" or aliquot, the mean size based on sizing all of the islets along with the size distribution should represent a significant step forward. De Vos, et al, 1998 observed that death of islets in capsules containing multiple islets or larger islets occurred first and suggested that it is inadvisable to transplant capsules with large or multiple islets. With the present invention, it is possible to separate out the large islets and capsules with multiple islets and test this observation using in vivo studies.

The analyses afforded by the present invention can be made inline at a very high rate (up to 1,000/sec) with the limitation being the flow rate and the rate at which the samples can be deflected by the jet system. The ability to simultaneously size and count the islets allows the rejection of islets and tissue that are too small to function as well as severely damaged islets. Very low laser power is used in the interrogation so the light beam will not harm the islets.

A number of researchers have recognized the importance of the capsule wall thickness on the diffusive resistance of the capsule and hence, on the failure of the encapsulated tissue. Necrosis appears to occur in the center of the islets indicating that insufficient nutrients are reaching the tissue (de Vos, et al, 1998). In addition, excessive wall thickness results in a limitation on the diffusion of waste material. Currently, only a small sample of the encapsulated islets may be examined to assess the capsule wall thickness and islet eccentricity within the capsule. Furthermore, the location of the islet within the spherical capsule is determined by chance. Available means do not allow the selection of capsules with adequate wall thickness and eccentricity of the islets because of the large number of islets required for large animal transplants.

The present invention has the capability of estimating the microcapsule wall thickness observed from two orthogonal directions. Microencapsulated islets with insufficient wall thickness over the entire capsule for adequate immunoisolation or that is too thick to allow diffusion of nutrients and biological waste may be rejected inline. These measurements are made in situ simultaneously with the other selection criteria and do not require additional manipulation of the sample.

In the early stage of development of the present invention, some concern was expressed over the possibility of clogging the system with the large number of blank capsules in the sample. However, the inlet and connections to the flow channel were revised so that the particles would not accumulate at sharp corners or changes in the size of the flow channel. Initial clogging did occur but after these design modifications the system was able run without clogging. Sample dilution to increase the average spacing between the solid particles also helps in preventing clogging and facilitating the sorting process.

Due to the large number of blank capsules that are mixed with the encapsulated islets and the requirement of deflecting a part of the flow in the neighborhood of the encapsulated tissue, there was a concern that this might result in the simultaneous deflection of blanks in the vicinity of the encapsulated tissue. The feasibility study for the present invention showed that it is possible to achieve good separation with approximately 20% of blanks with the encapsulated tissue. The original sample had more than ten times as many blanks as encapsulated tissue so this represented a significant improvement. A second or third pass through the system could be used to reduce the number of blanks to a few percent of the total number of encapsulated islets. Furthermore, a few blanks in the sample will not compromise the transplant. Most of the studies conducted have included significant numbers of blanks with the graft.

BRIEF DESCRIPTION OF THE DRAWINGS

FIG. 2 is a planar side view of the interrogation region of an alternate embodiment with a single upstream channel.

FIG. 5*a* is a cross sectional drawing of the beam path and components of a single interrogating laser.

FIG. 5*b* is a cross sectional drawing of the optical beams interacting with a particle containing an islet.

FIG. 5*c* is a cross sectional drawing of the optical beams interacting with a particle without an islet.

DETAILED DESCRIPTION OF THE PREFERRED EMBODIMENTS

Figure 1A:
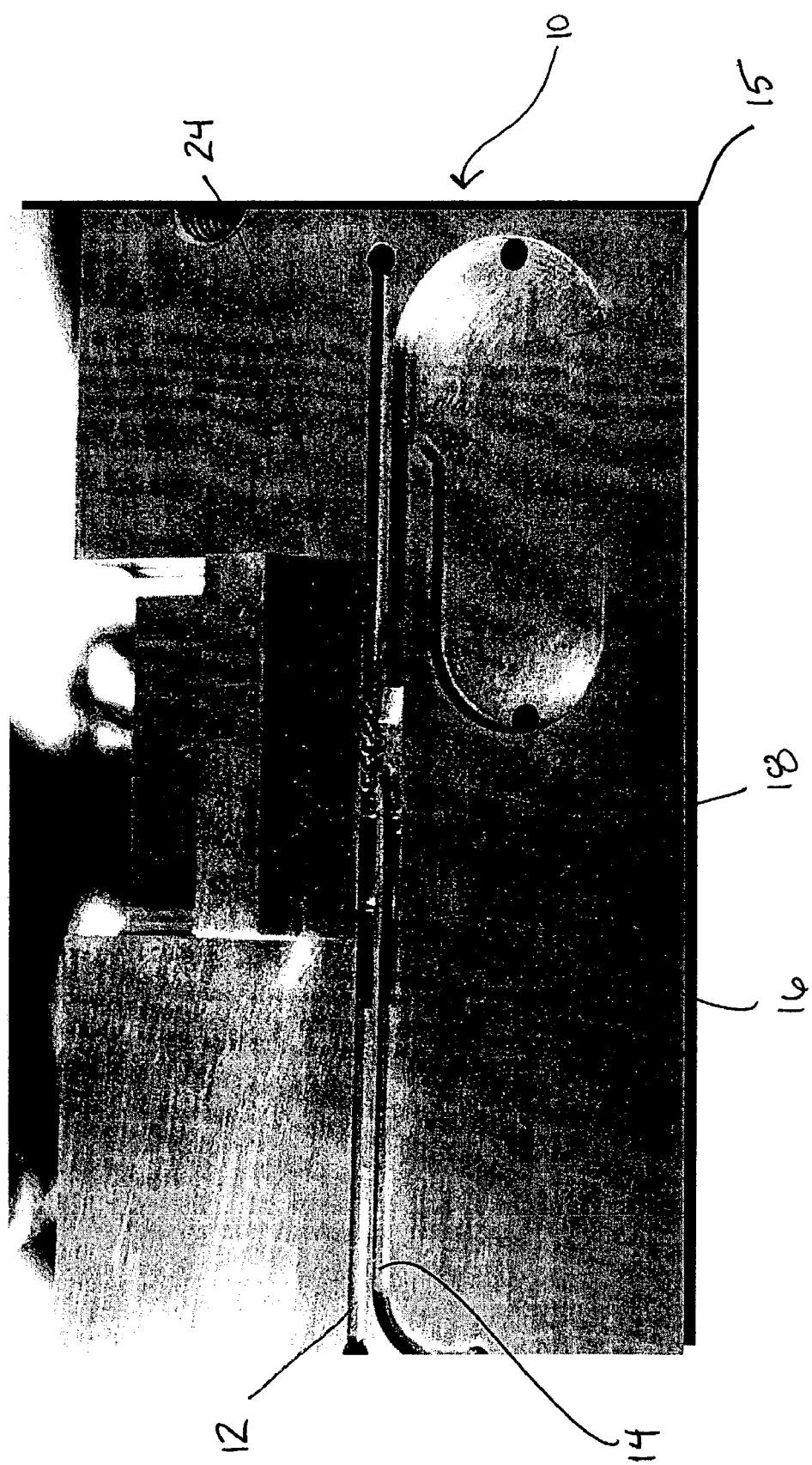
FIG. 1a is a perspective view of the sorter plate of the present invention showing the bifurcated stream channels of the preferred embodiment.

The present invention provides real-time automated electro-optical diagnostics for the evaluation and selection of successfully encapsulated cellular material from blank capsules, satellite particles, extraneous tissue, and other debris that may be present in the sample. The sample material is directed through a first channel in a fluid stream. A second channel, containing the identical fluid media, is disposed alongside the first channel. A window or opening, defined between the first and second channel, allows for the selective transfer of particles between the fluid streams. A sensor system is operably positioned along the first stream upstream of the window for diagnostic purposes. A fluid jet stream, responsive to the sensor system, deflects capsules from the fluid stream of the first channel through the window to the fluid stream of the second channel. Additional optical diagnostics provide information on the islet size and microcapsule wall thickness surrounding the islet. Non-selected material remains on its original course in the first channel. The non-selected material is either reevaluated or directed to a waste stream.

The process presently used to microencapsulate tissues for large animal transplants results in a large number of capsules with typically 5 to 10 blank capsules for every capsule containing the tissue. An excessive number of blank capsules is not desirable because they may interfere with the function of the transplant and produce a greater probability for immunological attack of the graft. Furthermore, because of the complexities associated with the encapsulation of such large numbers of islets (on the order of 1 million), there may be significant numbers of the islets that are not completely encapsulated, have insufficient capsule wall thickness for immunoisolation, or have wall thickness that is too large for adequate diffusion of nutrients to the encapsulated tissue, and they too are undesirable for the transplant. Encapsulation strategies that are currently used to overcome such problems include using double or triple encapsulations to increase the probability of ensuring adequate immunoisolation. However, the drawback is that it exposes the tissue to additional stress that may ultimately threaten the viability and functionality of the transplant and can result in excessive capsule wall thickness adversely affecting the diffusion dynamics. Therefore, it is helpful to perform diagnostic evaluation of the capsules prior to implantation to remove the material, which may threaten the viability of the transplant.

In a preferred embodiment of the present invention, the double layering process as described by Walsh in U.S. patent application Ser. No. 09/900,466, creates encapsulated islets for implantation. The present invention addresses these issues in that it permits the quality of each microcapsule to be assessed and to reject those capsules that do not meet pre-established criteria. Furthermore, it has been established that purified alginate capsules may not serve as a suitable substratum for cell attachment because mechanical imperfections on the surface of the microcapsule can provide sites for attachment and subsequent spreading of the growth from the cell anchorage. Fibrotic overgrowth is believed to be initiated once deposition of cellular material occurs. The present invention also provides for rapid assessment of the surface quality of each capsule in order to reduce the opportunity for such fibrotic overgrowth by removing capsule with poor surface qualities.

Flow Channel Geometry and Construction

In a first embodiment of the present invention, the sorter system 10 is illustrated in FIG. 1*a*. The sorter system 10 includes a sample channel 12 and a collection channel 14 which are disposed so as to extend generally parallel in the region extending immediately prior to the sensor region 16 through the region downstream of the fluid diversion system 18. Fluid window 24 is defined between the sample channel 12 and collection channel 14. Channel geometry upstream and downstream from this region may vary as long as laminar flow exists. Sample channel 12 contains encapsulated islets 20 and blank capsules 22 prior to fluid window 24. It is expected that blank capsules 22 will outnumber encapsulated islets 20 by 10:1 ratio. After fluid window 24, sample channel 12, ideally, contains blanks 22 while collection channel 14 transports islets 20 to collection reservoir 15.

The channels are each made from stainless steel. All fittings are medical grade and FDA approved so as to ensure that no contamination is produced in the sample media. The surfaces are polished and flat to allow sealing with the window without additional sealing material or gaskets, which may add to the risk of contamination. Each channel is designed for easy assembly so that it may be stripped down and sterilized after each sorting run. Windows are provided at the interrogation window 16 as well as downstream to allow evaluation of the sorting efficiency. A pneumatic feed system will be used with precisely controlled pressure on the supply and collection vessels. Clean oxygenated air will be used to supply the pressure.

Alternatively, a molded plastic channel system could be adopted following the same layout as described in FIG. 1*a*. This would reduce the cost and time for cleaning a stainless steel channel after each use. A plastic system could be discarded after each sorting run. Some components of the optical diagnostics system may also be fabricated as part of the unit and will also be disposable. This includes any components that will come in contact with the encapsulated tissue sample.

Reproducing the incubator conditions within the channels 12 and 14 will help preserve islet viability. The flow channel includes thermostatically controlled heaters that will maintain all of the components at the desired temperature. The oxygen level in the supply air will also be maintained at the desired level. Computer controlled pressure sensors and regulators will prevent any overpressure in the system.

The sample channel 12 is initially diluted to increase the average spacing between the encapsulated particles 20 and the blanks 22. It is essential that the flow in channels 12 and 14 is kept laminar to minimize the potential for impact damage to the capsules. Furthermore, the liquid boundary layer in the channel minimizes the shear stress on the capsules.

Figure 1B:
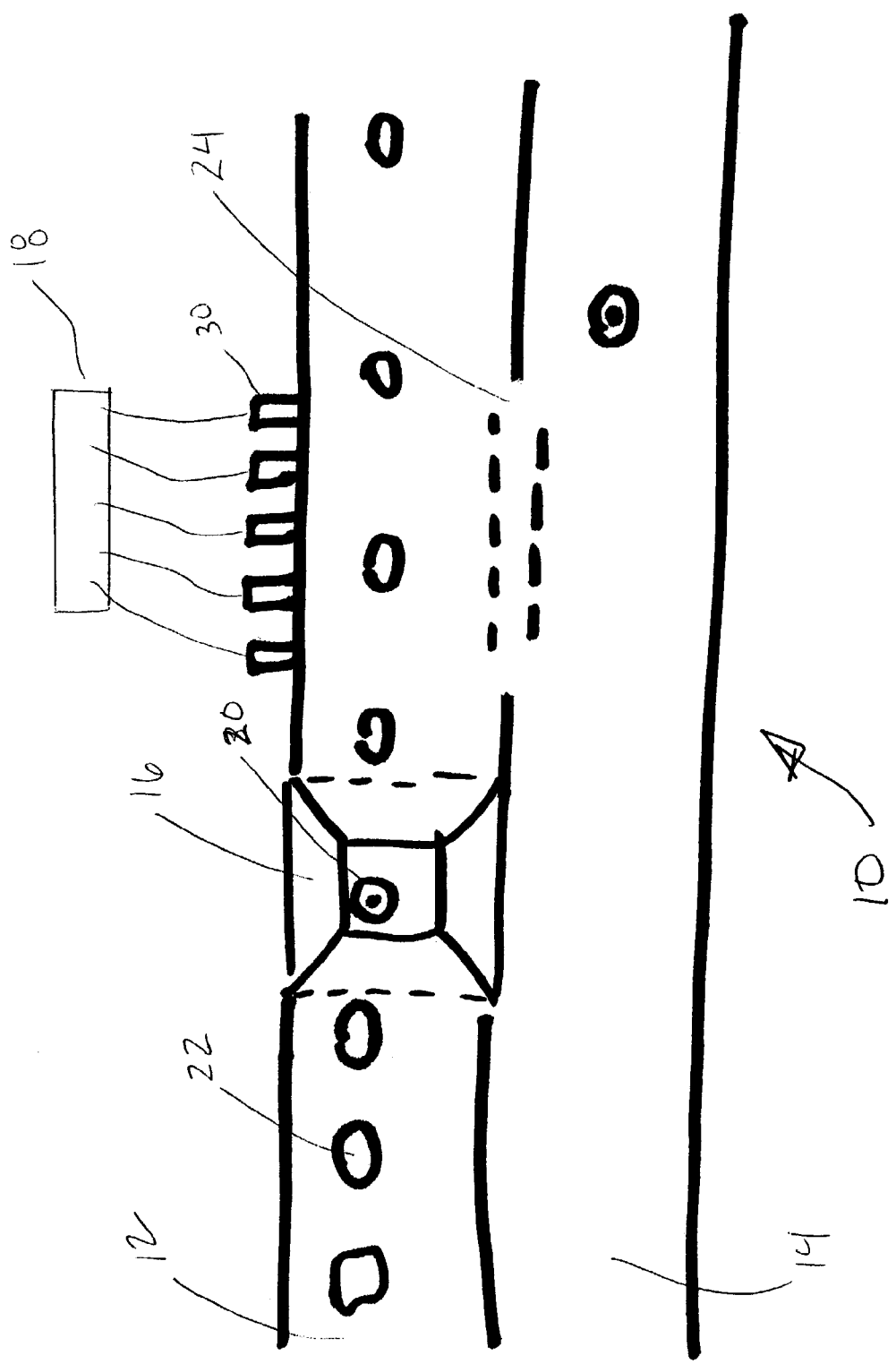
FIG. 1b is a planar side view of the interrogation region and fluid window of a preferred embodiment.
Figure 1C:
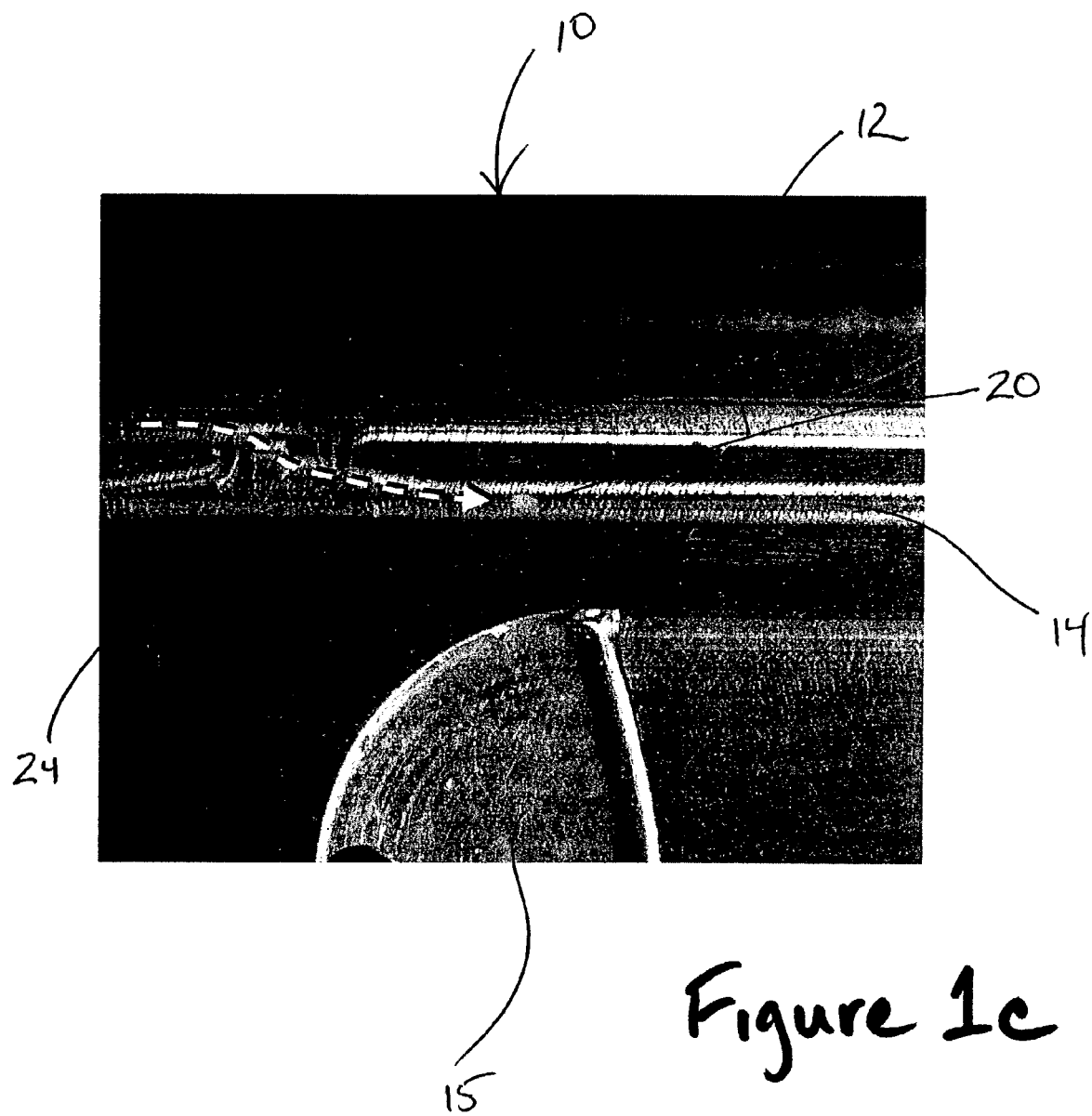
FIG. 1c is perspective view of the fluid diversion system with jets firing.

Downstream from interrogation window 16 is fluid window 24 that is an opening between channel 12 and 14 (See FIG. 1b). The laminar flow layer running along the walls of the respective channels 12 and 14 prevent cross flow unless triggered by the plurality of jets 30 of the fluid diversion system 18. Once an encapsulated particle 20 is recognized, the fluid diversion system 18 fluidly forces the encapsulated particle 20 into the laminar boundary layer (See FIG. 1c). Upon breaching the boundary layer, encapsulated particle 20 is actually pulled into collection channel 14 after escaping the shear stress along the channel wall.

An increase in flow velocity may create turbulence in the channels. While a higher flow speed will allow a faster sorting rate, it may compromise the islet viability. High-speed laminar flow requires smooth inlets and surfaces in the channel and a minimized length of the channel to prevent tripping the flow to turbulent at high flow Reynolds number. Controls systems maintain the relative flow rates in sample channel 12 and collection channel 14 to optimize the sorting.

This complex fluid dynamic system is continuously monitored to immediately detect any change in the flow conditions. It is expected, due to the particulate nature of the sample, that clogging and other changes to the flow may be expected. Thus, additional monitoring stations downstream of the channel bifurcation will be used to count the encapsulated tissue samples in each channel. This provides quasi-real-time information on the sorting efficiency.

Figure 1D:
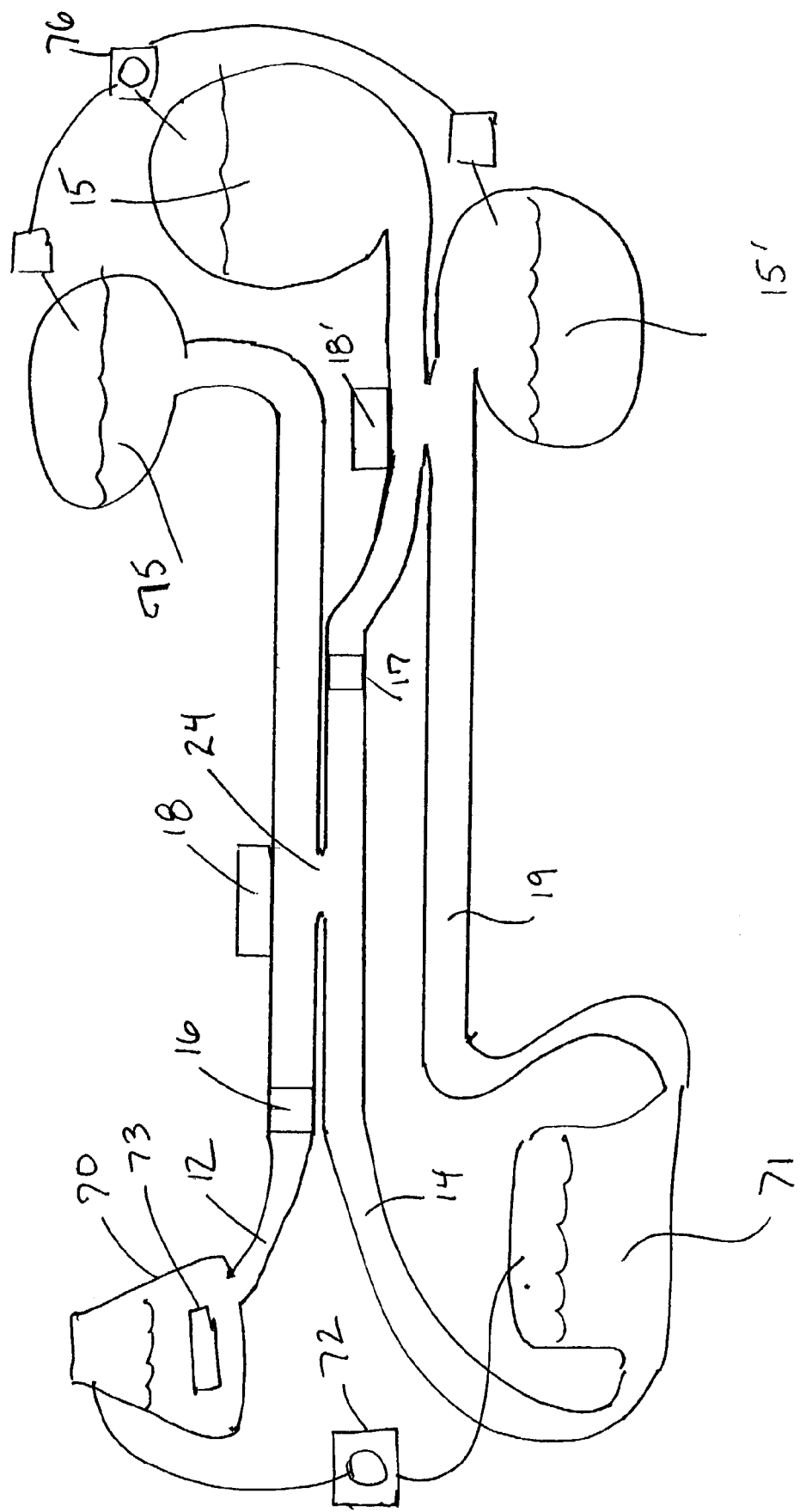
FIG. 1d is an alternate embodiment with bifurcated channels and a second interrogation region and fluid diversion system mounted on the collection channel.

Alternate embodiments based on the bifurcated channel illustrated in FIG. 1a may be incorporated to provide further capsule evaluation. FIG. 1d illustrates a second sensor region 17 along collection channel 14 downstream from fluid window 24. It is expected that the majority of capsules 20 in channel 14 will be acceptable so fluid diversion system 18' will force unacceptable capsules into secondary collection channel 19 and reservoir 15'.

It is envisioned that alternate channel geometries, for example as illustrated in FIG. 2, may be incorporated into the present invention. FIG. 2 illustrates the use of a curved sample channel 52. The curved flow provides a centrifugal force that carries the encapsulated particles 20 to the outer part of flow channel 52. The encapsulated particles 20 and blanks 22 flow through the interrogation window 16. Channel 52 is bifurcated into a collection channel 54 and a waste channel 56 at bifurcation point 60. Jets 30 must have sufficient control to divert encapsulated particle 20 before reaching the turbulent zone immediately upstream of bifurcation point 60. Blanks 22 are left to continue into waste channel 56. Downstream monitoring along waste channel 56 may result in a second or even third pass through the system if encapsulated particles are discovered.

Pneumatically Controlled Flow System

The flow rate in the channel is easily controlled by setting the pressure differential between the supply and collection vessels. As illustrated in FIG. 1d, supply vessel 70 is fluidly connected to supply channel 12 and supply vessel 71 is fluidly connected to supply channel 14 and examination channel 19. An air pressure generator 72 is pneumatically connected to both supply vessels 70 and 71 for creating and maintaining the desired pressure. Both collection vessels 15 and 15' and waste vessel 75 are also pneumatically joined and monitored by pressure monitor 76.

Alternatively, syringe pump are used to drive the liquid with the encapsulated islets into supply channel 12. This approach does not easily allow the processing of larger volumes (1 to 10 liters) of the media containing the encapsulated islets. The number of capsules per cc of media must be low enough to ensure the separation between the particles is at least a few mm as they pass through the flow channel. If there is an unexpected blockage, syringe pumps can generate a very high pressure which may damage the islets.

Using the pneumatic approach described above with respect to FIG. 1d to drive the sample ensures that the pressure on the sample does not become excessive. Typically, a differential pressure of a few psi is adequate. A large volume liquid can be handled with minimal user intervention. Computer controlled valves and pressure transducers allow continuous monitoring of the system and accurate control of the flow in the channel. Since there are no moving parts, there is little potential for mechanical stress or damage to the sample. A stirring mechanism 73, such as a magnetic stirrer, is used to keep the encapsulated tissue and blank capsules dispersed and floating in the oxygenated supply vessel 70.

Electro-Optical Interrogation

Figure 3:
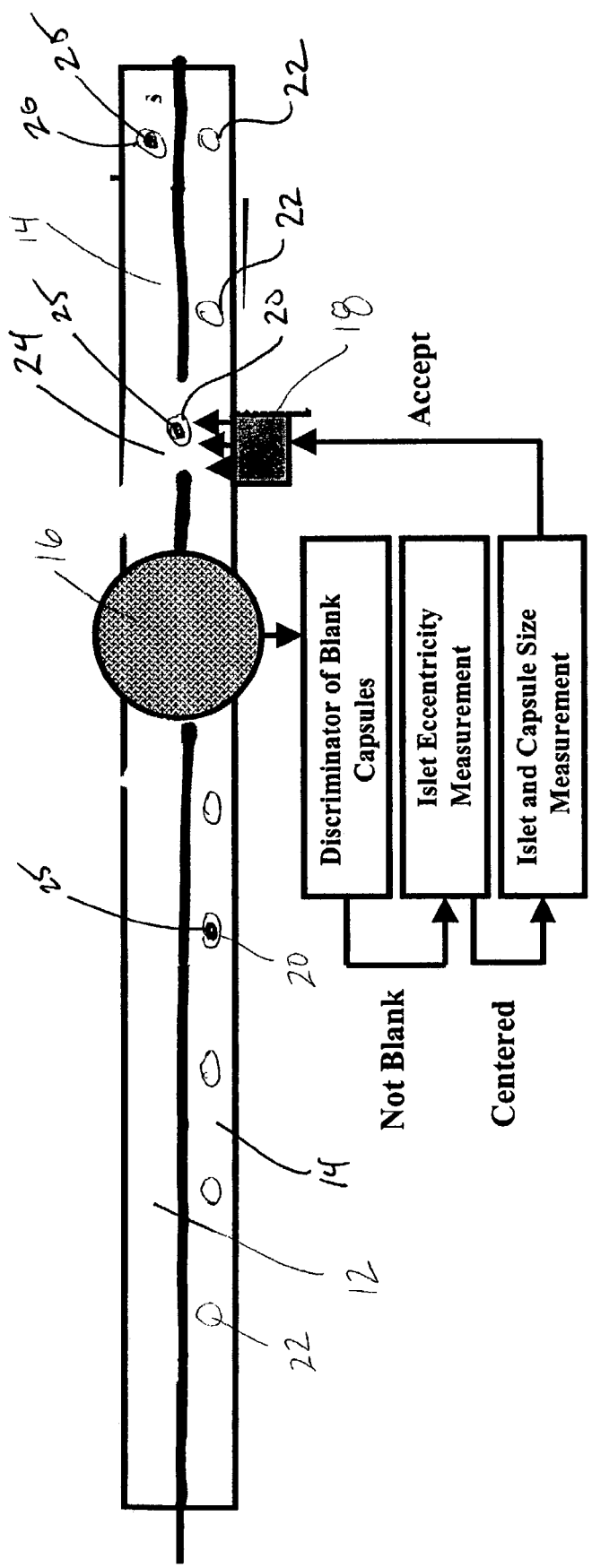
FIG. 3 is a flow chart combined with a planar side view of the interrogation region of the present invention.

As illustrated in FIG. 3, three unique forms of interrogation are performed while the sample material flows through interrogation window 16. First, the present invention determines whether or not the sample is a blank 22 or if it contains an islet 25. Secondly, the encapsulated particles 20 are examined to determine whether the islet 25 is centered within the capsule. Third, the islet 25 and capsule 20 are measured. The second and third steps may be repeated or even initiated once the encapsulated particle 20 has been diverted into collection channel 14.

Figure 4:
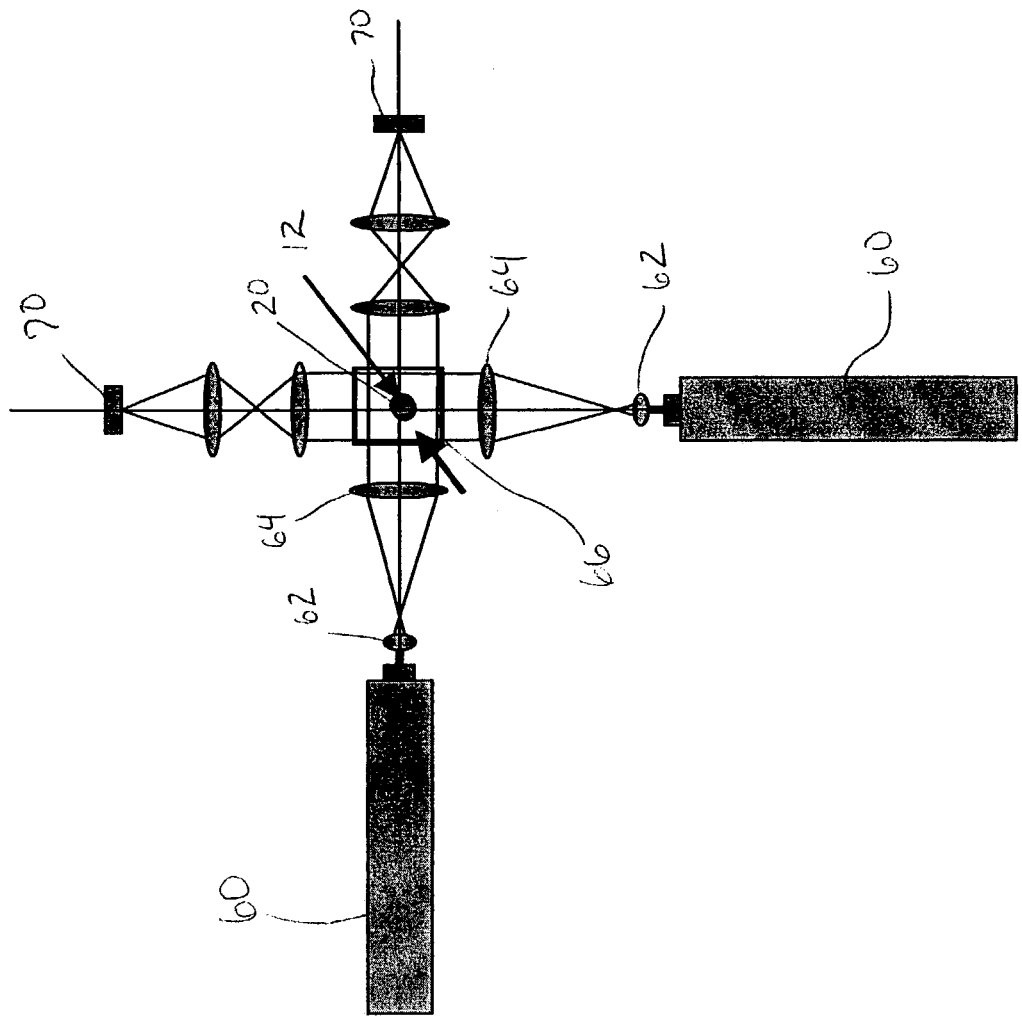
FIG. 4 is a cross sectional view of the orthogonal laser interrogation system.

A first embodiment of the electro-optical interrogation system of the present invention is illustrated in FIG. 4. A solid-state laser diode 60 is used as a light source. The beam propagates through expander 62. The expanded and collimated beam is directed through slit aperture 64 and through laser opening 66 which spans flow channel 12. In a first embodiment the slit aperture 64 is 50 micrometers wide and 2 millimeters long. The resultant beam forms a light sheet with a uniform beam profile. The light sheet fills the interrogation window 16. A solid-state photo detector 70 is disposed to detect the transmitted light sheet.

Detection of Encapsulated Particles

The first step is removing the blank capsules from the sample of encapsulated islets. This part of the process does not require 100% reliability since in past studies blanks, have been transplanted along with encapsulated islets and, to-date, failures have not been directly correlated with an excess of blank tissue. The present invention provides for 90% separation of the blanks and extraneous material from the sample in a single pass through the channel and >99% separation using a dual-pass system.

An electro-optical method of the present invention enables the detection and counting of the encapsulated particles 20 as they pass the interrogation window 16. Since the blank capsules 22 are transparent and have an index of refraction only slightly greater than the media, they are essentially invisible to the appropriately designed detection system and hence, are not detected. This is significant since there are a much larger number of blanks 22 than encapsulated particles 20 so this relieves the load on the sorting system logic. The islets 25 or other tissue is opaque or diffusely scatter the incident light so a strong signal is produced as they pass the interrogation window.

FIG. 5a illustrates this principle in one dimension. The presence of an islet obscures the light, FIG. 5b, while a blank capsule 22, as illustrated in FIG. 5c allows the light to pass unobstructed. The depth (degree of laser beam obscuration) of the signal is related to the size of the islet 25. Calibration is used to enable a quantitative measure of the size of islet 25. The presence of islet 25 reduces the transmitted laser light intensity depends on the obscuration of the light sheet.

A second dimension of the islet 25 can be determined from the duration and shape of the signal. The duration of the obscured signal can then be used to measure the islet 25 since the light intensity decreases when the leading edge of the islet 25 passes through the light sheet and it returns to an ambient condition after the islets passes. Because the islets 25 are not spherical, it is preferable to conduct this same evaluation from an orthogonal direction, as illustrated by FIG. 4; however, this is not absolutely necessary. Because the islets will pass the sensor systems in random orientations and because all of the islets are interrogated, a statistically measured size distribution from a single direction will be representative of the actual size distribution of islets in the sample.

The detection electronics utilizes a signal threshold detection system that can be adjusted to only detect tissue samples larger than a specific size. The system can detect tissue samples within 10 microseconds and at a very high repetition rate (>10,000/sec) so it is not be the limiting component in the sorting system. In one embodiment, the detection systems are disposed at three or more locations in the channel to monitor the sorting performance and directly measure the sorting efficiency.

Islet Eccentricity and Measurement

Occasionally, microcapsules show exposed tissue or islets 25 too close to the capsule walls. Such conditions may excite an immune reaction by the host or may provide insufficient protection of the islets and compromise the viability of the entire transplant. Thus, the present invention provides optical means to detect defective encapsulations and reject these capsules from the sample. The islets 25 are approximately 150 µm in mean diameter but with a relatively large variation in size. Required capsule wall thickness is generally considered to be between 20 and 200 µm. However, it also depends upon the porosity of the alginate material used. Thus, additional optical means are required to assess the particles.

In a first embodiment, the actual microscopic image of each microencapsulated islet 25 is recorded with a miniature charge coupled device (CCD) camera and analyzed to obtain the islet size and capsule wall thickness. Since only the encapsulated tissue samples are detected, the CCD need only process these images online. The channel is small enough (1 mm by 1 mm) so the microcapsules would pass within the depth of field of the optics providing sharp images. To obtain a reasonable estimate of the islet 25 and capsule 20 dimensions, a 128 by 128 pixel CCD with 8-bit quantization may be used. The capsules 20 typically have a mean diameter of 300 µm. The islet 25 dimensions and capsule wall thickness can be resolved to +/−10 µm.

This embodiment provides for the recording and transfer of 16 k bytes of data to a DSP chip for image processing. The islet size, eccentricity, and capsule wall thickness are established in approximately 1 millisecond in order to make the decision to accept or reject the sample before the bifurcation point. The 128 by 128 pixel images could be reduced to a grid pattern with, for example 10 pixels spaces between the grid lines. This grid system significantly reduces the number of bytes of information that need to be processed.

An alternate embodiment involves laser light scattering interferometry. A plane coherent light wave incident upon a transparent particle is partially reflected and refracted at the interface of the transparent medium. The refracted light is deflected from its incident direction according to Snell's law and the phase of the light is affected since the light speed is different in the medium than in the air. Since the laser light used is coherent and essentially consists of approximately a single wavelength and frequency that is relatively stationary in time and space the light deflected by the mechanisms of refraction and reflection will interact. This interaction is well known as light interference, which produces bright and dark fringes where the light interferes constructively and destructively, respectively. Encapsulated tissue will produce this light scattering phenomenon, and the resulting interference pattern produces a signature that can be used to infer information on the quality of the encapsulation.

FIG. 5a shows the schematic diagram of the optical set up used in the present invention. A diode-pumped solid-state laser is used as the light source. The beam is expanded and directed through the window of the first channel. The light scattered by the microencapsulated tissue is directed onto a viewing screen with a hole or aperture that allows the undeflected part of the laser beam to pass without producing excess background light. The far field (approximately 500 mm from the capsule) laser light scattering pattern is imaged by a digital camera. The light scattering signature for the microcapsule is then imaged and transferred to a computer for image analysis, storage and presentation. The decision to keep or reject a particular imaged capsule is preferably made within a millisecond and a control signal is generated to the jet deflection system. When the capsule is moving in the fluid stream, a fast shutter is required for the digital camera. An intensified CCD array camera can meet this requirement with a shutter speed providing for less than a one microsecond exposure.

Figure 6:
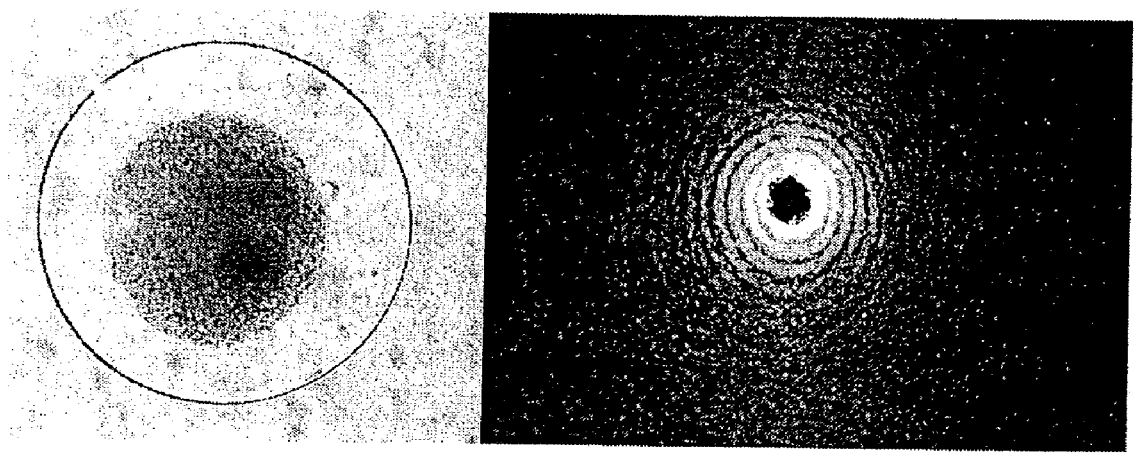
FIG. 6 is a photograph of an islet centered within a capsule and the resulting fringe pattern produced by optical interrogation.

FIG. 6 shows the case of a nearly perfect encapsulation with approximately uniform capsule wall thickness around the tissue. Note that the corresponding far field interference fringe pattern is nearly symmetric with approximately uniform spatial frequency (spacing between the fringes). Also, note that the dark spot in the center of the interference fringe pattern is simply a hole in the screen allowing the laser beam to pass through without overwhelming the light scatter pattern.

Figure 12:
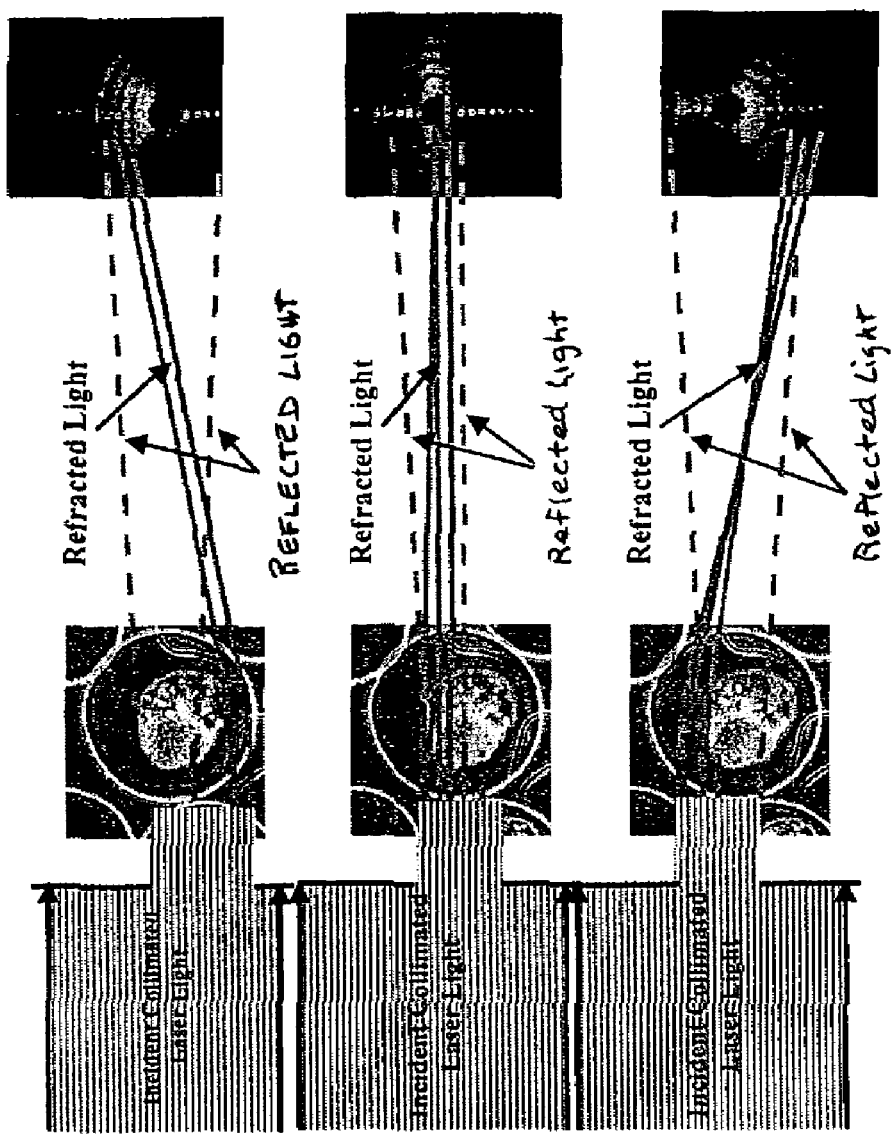
FIG. 12 is a schematic showing the light scattering results of optical interrogation as an encapsulated islet passes through the light sheet formed by the slit aperture.

In this embodiment, the current islet detection system uses a slit aperture on the laser beam that is 100 µm wide and spans the flow channel. Thus, the encapsulated islets are illuminated by a sheet of laser light that is 100 microns wide as they pass the interrogation area. This effect is illustrated in FIG. 12. Note that as the particle passes the slit, the laser light sheet will scan the capsule. FIG. 12 shows the process along with the light scattering pattern. There are some fortunate benefits in this process. The interference fringe pattern produced by the encapsulated islets appears to sweep the interference pattern as the encapsulated islet moves past the slit aperture. As will be seen in subsequent figures, if the islet is not encapsulated, no interference fringe pattern is formed over that region of the islet. If it is a blank capsule, no significant interference pattern forms so this is an additional test for blanks, if blanks happened to be detected by the detection electronics.

Figure 7:
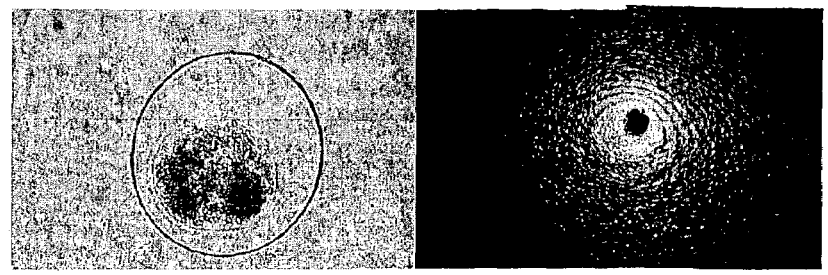
FIG. 7 is a photograph of an offset double encapsulated islet and the resulting fringe pattern produced by optical interrogation.

FIG. 7 shows the case wherein the tissue is slightly off-center in the capsule and the interference fringe pattern has a corresponding asymmetry which resembles a contour map but the fringe spacing is inversely proportional to the capsule wall thickness.

Figure 9:
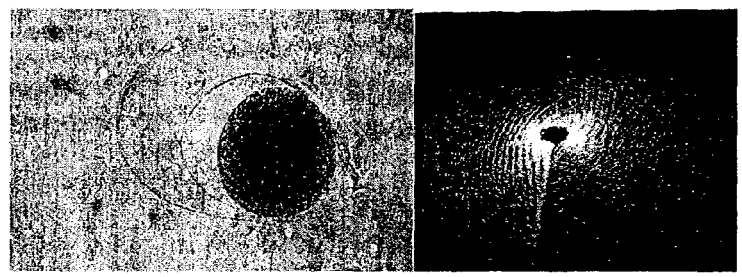
FIG. 9 is a photograph of a broken capsule with an offset islet and the resulting fringe pattern produced by optical interrogation.
Figure 8:
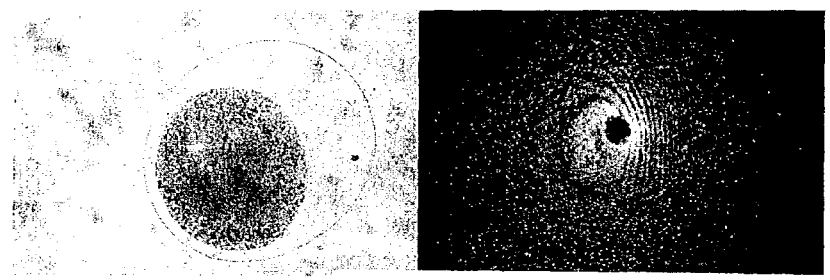
FIG. 8 is a photograph of an offset islet within a capsule and the resulting fringe pattern produced by optical interrogation.

In the extreme case of a very thin capsule wall thickness on one side, the interference fringe pattern becomes very wide and almost disappears into the background laser light speckle pattern as illustrated by FIG. 8. FIG. 9 illustrates the case of an islet with a broken capsule so that material has escaped. This information is relatively easy to detect and used as a quality determination as to whether the sample will be discarded from further consideration. A quantitative measure of the capsule wall thickness distribution around the tissue, which includes processing the signal and deciding whether or not to keep or reject the sample occurs within 0.1 milliseconds.

Figure 10:
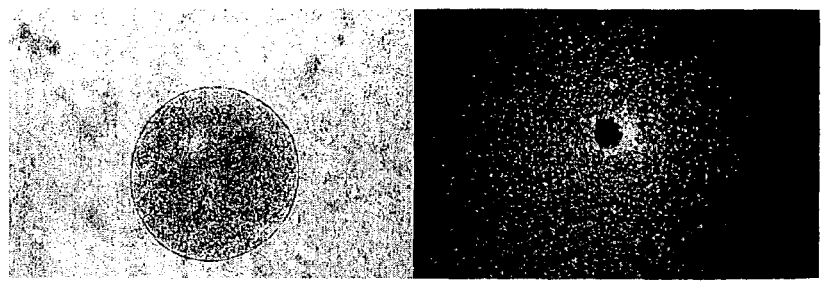
FIG. 10 is a photograph of an islet without a capsule and the resulting fringe pattern produced by optical interrogation.
Figure 11:
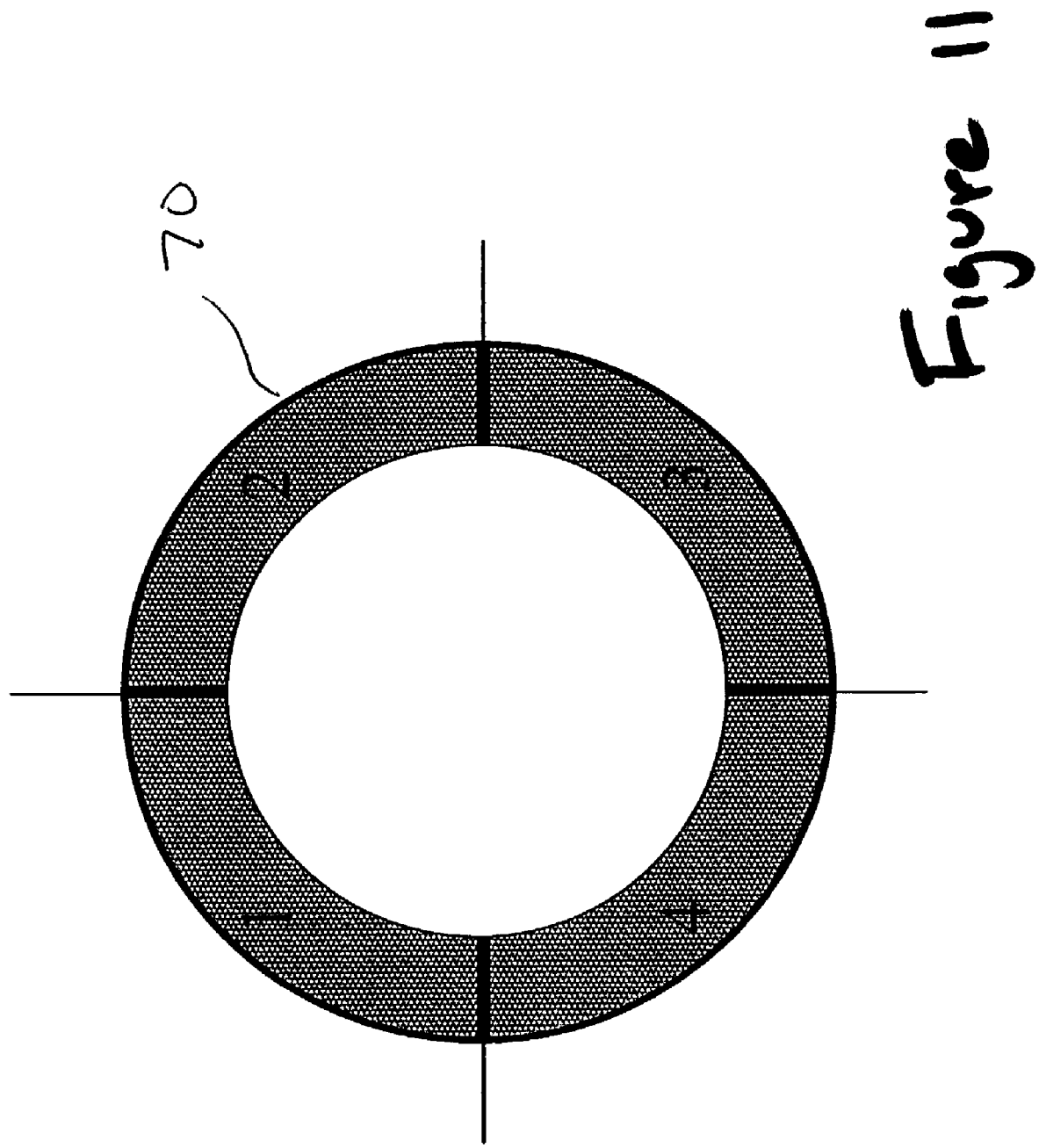
FIG. 11 is a cross sectional view of the quadrant system for image analysis.

In order to extract information concerning the quality of encapsulation in the short time presented a quadrant detector scheme is used. The light scatter from the particle is measured by a quadrant detector 70 in each of the four quadrants (See FIGS. 5a and 11). If the particle is eccentric, the light scatter is different within the four quadrants. FIG. 10 illustrates an islet without encapsulation. This produces a relatively uniform intensity in the light scattering pattern so the intensity in each quadrant will remain approximately equal as the islet moves past the laser light sheet whereas the pattern changes with time if a capsule is present, as shown in FIG. 12.

Higher order signal processing may be used to obtain quantitative information on the capsule wall thickness. If the scattered light pattern is recorded with a 128 by 128 pixel CCD array, the suitable grid pattern can be processed to obtain detailed information on the encapsulation. The spatial frequency of the interference fringe pattern is approximately equal to the capsule wall thickness measured along radial lines.

The most effective and reliable method to obtain the spatial frequency of the pattern is with the mathematical analysis known as the Fourier transform. The Fourier transforms are very effective in locating sinusoidal signals even under low signal-to-noise (SNR) conditions. Digital signal processor (DSP) chips are available that can compute the Fourier transform using the fast Fourier transform (FFT) algorithm.

The present invention allows for counting and sizing the islets online at a very high rate (up to 1,000/sec). The method analyzes the sample from two directions to obtain an equivalent diameter (islets are not spherical so a true size definition would require more than one dimension) from two orthogonal projections. This ability to simultaneously size and count the islets allows for the rejection of islets and tissue that are too small to function as well as those severely damaged islets.

The method for sizing the islets includes a calibration methodology using islets having a full range of morphology and size. This is carried out utilizing histological analyses and comparing the results. The present invention will result in an equivalent islet diameter of within +/−10%. The size distribution is also recorded along with the count of the number of islets in the sample.

Jet Deflection System

The present invention provides for reliable sorting of the capsules through the jet deflection system. It is envisioned that the deflection system will have the means to vary the valves and jets with respect to response time, delay, duration, and jet momentum. Circular jets or jet slits can be utilized to span the channel. Jet sheets will produce a shorter stream wise perturbation and will prevent capsules slipping by the deflection system. It is understood that the jets must have adequate momentum to deflect the encapsulated tissue but not have excess momentum that could damage the surface of the capsules due to impact with the channel wall.

In a first embodiment, the present invention incorporates high-speed valves supplied by a manifold and vessel of media under selected pressure (typically 2 psi to 30 psi) to form jets which allows for the use of the media as the fluid which deflects the selected samples into the collection channel without excess stress. Five jets are lined up in the flow so each jet can contribute a part of the deflection force and hence, minimize the impact and acceleration on the capsule. The jet pressure, timing, and duration are all precisely selectable and can be optimized for adequate deflection and minimal stress on the sample. In addition, it is also possible to use the valve system to provide suction on the opposite side of the channel for faster response and reduced deflection pressure on the capsules.

Firing of the jets 30 must be timed so as to divert the encapsulated particle 20 into collection channel 14. This is particularly problematic due to the fact that the particles in the stream are neither uniform in size, shape or mass and firing of the jets may cause some changes in the flow speed of the channel. Therefore, the speed of each individual particle must be determined prior to reaching the fluid diversion system 18. Particle flow speed in channel 12 can be accurately measured by optically illuminating the particle through a pair of slits a known distance apart. This interrogation takes place within sensor region 16. By measuring the time between peak signal pulses and knowing the slit separation, the flow speed of the particle is determined. The size of the particle along the flow direction can also be measured by the width of the signal. Jet 30 firing sequences can then be calculated for each individual particle.

For the preferred embodiment in operation, the fluid carrying the microencapsulated tissue enters channel 12 and follows the path to the fluid window 24. The liquid is supplied by pressurizing the flasks with clean air to approximately 5 psig. It should be noted that this method would also work with microcapsules or other materials in a gas stream. In the present application, the channel was 1 mm by 1 mm cut in a metal plate and closed by a window to allow observations of the flow field.

Fluidic jets 30 are provided in the neighborhood of the fluid diversion system 18. The flow in the bifurcated channels 12 and 14 shown in FIG. 1 carry the waste material (blank microcapsules and other debris) and the microencapsulated islets, respectively. The relative flow rates in channel 12 and 14 could be adjusted by precise adjustments of the pressure in the collection vessels.

An electro-optical sensor port 16 in the channel is provided immediately upstream of the fluid window 24 that is used to detect the encapsulated tissue and to evaluate the quality of the encapsulation. Encapsulated tissue passing the detector port is detected which triggers the jet deflection system. Estimating the wall thickness of each capsule to within +/−10 microns is achieved by observation from two orthogonal directions. These measurements are performed online simultaneously with the other evaluations. The required low-resolution CCD's, data transfer, and the fast Fourier transform (FFT) is completed within the observation time of approximately 2 milliseconds.

In a first embodiment, the deflection system is comprised of 5 equally spaced jets that are 0.75 mm in diameter allowing the jet flow to enter orthogonal to the stream. Miniature valves that can open in 0.25 milliseconds and can be opened for a preset duration control the jets. An electronics circuit was designed using CPLD (Complex Programmable Logic Device) chips that allow programming of any number of strategies for controlling the jets. The jets 30 can be fired at selected delay times after the detection of the islet, in sequence, simultaneously or other arrangements. The duration of each jet flow may also be precisely set so complete electronic control of the deflection system is available.

Additional detection systems can be installed downstream on sample channel 12 and collection channel 14 to enable reliable counting of the number of microencapsulated tissue samples in each channel. This will provide a direct evaluation of the efficiency of separation as well as a count of the number and size of encapsulated islets.

Up to 1000 capsules per second can be evaluated per sorter unit and because of the modest cost of components, 10 units or more could easily be operated in parallel allowing all of the 10,000,000 capsules to be analyzed in approximately 20 minutes.

The complete disclosures of the patents, patent applications and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein.

What is claimed:

1. An automated system for evaluation and selection of capsules a minority of which contain encapsulated cellular material comprising:
    a first channel through which a first fluid stream containing capsules is introduced into the system and will exit from the system if undeflected;
    a second channel through which a second fluid stream is introduced;
    a window defined between the first channel and the second channel across which the first fluid stream is directly adjacent the second fluid stream;
    a sensor system operably positioned along the first channel upstream of the window, the sensor system equipped to image the minority of the capsules which contain encapsulated cellular material from among the capsules contained in the first fluid stream; and
    a fluid jet system pulsed responsive to a control system coupled to the sensor system that identifies the minority of capsules which contain encapsulated materials and controls the fluid jet system for selectively deflecting the minority of the capsules which contain encapsulated cellular material from the first fluid stream across the window and into the second fluid stream such that fluid flow disturbance of the first fluid is generally created only when a capsule containing cellular material is detected by the sensor system,
    wherein a majority of the capsules not containing cellular material persists flowing through the first channel through which the first fluid stream containing capsules is introduced, without creating a fluid flow disturbance of the first fluid that affects imaging of the capsules by the sensor system.

2. The automated system of claim 1, wherein the fluid jet system comprises a plurality of impulse jet nozzles which are sequentially fired to deflect capsules from the first fluid stream across the window and into the second fluid stream.

3. The automated system of claim 1, wherein the control system determines whether any portion of the cellular material is outside the capsule as part of a determination of whether to selectively deflects the capsule.

4. The automated system of claim 1, wherein the first fluid and the second fluid are cell culture liquid media that are oxygenated and temperature regulated to accommodate the cellular material.

5. The automated system of claim 1, wherein the sensor system includes at least one radiation source having an output which is oriented to decrease back reflection.

6. The automated system of claim 5, wherein the radiation source includes a polarization filter before the output.

7. The automated system of claim 5, wherein the radiation source is oriented at an angle other than normal to the first channel.

8. The automated system of claim 1, wherein the encapsulated cellular material is contained within capsule having a radius of between 10 to 500 microns and the first channel has cross-sectional dimensions that are four to eight time the radius of the capsules.

9. The automated system of claim 1, further comprising a first supply vessel fluidically coupled to an input of the first channel, a second supply vessel fluidically coupled to an input of the second channel and a first collection vessel fluidically coupled to an output of the first channel and a second collection vessel fluidically coupled to an output of the second channel and a flow rate of the first fluid stream and the second fluid stream is established by creating a pressure differential between the first and second supply vessels and the first and second collection vessels.

10. The automated system of claim 9 wherein the first and second supply vessel are connected to a first air pressure system and wherein the first and second collection vessels are connected to second air pressure system and wherein the pressure differential between the first air pressure system and the second air pressure system is used to establish the flow rate.

11. The automated system of claim 9 wherein the first supply vessel includes a means for stirring a first fluid containing the capsules to disperse the capsules within the first fluid stream.

12. An automated system for evaluation and selection of encapsulated cellular material comprising:
    a main channel through which a fluid stream containing capsules is introduced;
    a control system including a sensor system operably positioned along the main channel, the sensor system equipped to image a minority of the capsules containing cellular material from among the capsules contained in the fluid stream;
    an outlet channel fluidically coupled to the main channel; and
    a fluid jet system operably positioned along the channel downstream of the sensor system, wherein the fluid jet system comprises a plurality of impulse jet nozzles arranged for sequential pulsing under control of the control system, each jet nozzle in the plurality of impulse jet nozzles configured to generate a fluid jet characterized by a jet momentum, the jet momentum calculated so that upon sequential pulsing, paired pulsing, or pulsing in unison of the impulse jet nozzles each of the minority of capsules containing cellular material is selectively deflected from the main channel into the output channel without generally contacting the main channel or the output channel and without generally causing a fluid flow disturbance in the fluid stream flowing in the first channel that would otherwise disrupt the imaging of the capsules, such that the capsules other than the minority of capsules containing cellular material remain in the fluid stream flowing in the main channel.

13. An automated system for evaluation and selection of encapsulated cellular material comprising:

a main channel through which a fluid stream containing capsules is introduced;

a control system including a sensor system operably positioned along the main channel that images the capsules, the control system evaluating the images to determine whether any portion of the cellular material is outside the capsule;

an outlet channel fluidically coupled to the main channel; and a fluid jet system operably positioned along the channel downstream of the sensor system and pulsed in response to the control system based on the determination as to whether any portion of the cellular material is outside the capsule in order to move the capsule from the main channel to the outlet channel while reducing disturbance of the fluid stream with respect to the sensor system.

* * * * *